(12) United States Patent
Veeger et al.

(10) Patent No.: US 8,252,847 B2
(45) Date of Patent: Aug. 28, 2012

(54) SKIN PROTECTION COMPOSITIONS, IN PARTICULAR CREAM TO PROTECT AGAINST COLD

(75) Inventors: Marcel Veeger, Goch (DE); Petra Allef, Krefeld (DE)

(73) Assignee: Evonik Stockhausen GmbH, Krefeld (DE)

( * ) Notice: Subject to any disclaimer, the term of this patent is extended or adjusted under 35 U.S.C. 154(b) by 0 days.

(21) Appl. No.: 12/514,326

(22) PCT Filed: Nov. 9, 2007

(86) PCT No.: PCT/EP2007/009726
§ 371 (c)(1),
(2), (4) Date: May 11, 2009

(87) PCT Pub. No.: WO2008/055692
PCT Pub. Date: May 15, 2008

(65) Prior Publication Data
US 2009/0318570 A1    Dec. 24, 2009

(30) Foreign Application Priority Data
Nov. 10, 2006  (DE) ................ 10 2006 053 360

(51) Int. Cl.
*A61K 8/02* (2006.01)
(52) U.S. Cl. ......... 514/937; 514/941; 514/943; 424/401
(58) Field of Classification Search ........... 424/401, 424/70.11
See application file for complete search history.

(56) References Cited

U.S. PATENT DOCUMENTS

| | | | |
|---|---|---|---|
| 5,653,989 A * | 8/1997 | Sattler ................. 424/401 |
| 6,376,438 B1 | 4/2002 | Rosenberger et al. |
| 6,471,983 B1 | 10/2002 | Veeger et al. |
| 6,489,275 B1 | 12/2002 | Veeger et al. |
| 6,649,577 B1 | 11/2003 | Bleckmann et al. |
| 7,163,916 B2 | 1/2007 | Allef et al. |
| 7,241,452 B2 | 7/2007 | Veeger et al. |
| 7,297,675 B2 | 11/2007 | Allef et al. |
| 2003/0235539 A1 | 12/2003 | Mongiat et al. |
| 2004/0047828 A1 | 3/2004 | Buenger et al. |
| 2004/0170592 A1 | 9/2004 | Veeger et al. |
| 2004/0247536 A1 | 12/2004 | Chaudhuri |
| 2005/0031580 A1 | 2/2005 | Allef et al. |
| 2005/0124705 A1 * | 6/2005 | Schreiber et al. ........... 516/53 |
| 2005/0201955 A1 | 9/2005 | Bunger et al. |
| 2006/0165627 A1 * | 7/2006 | Allef et al. ........... 424/70.11 |
| 2006/0182690 A1 | 8/2006 | Veeger et al. |
| 2006/0198859 A1 | 9/2006 | Allef et al. |
| 2006/0204468 A1 | 9/2006 | Allef et al. |
| 2007/0041927 A1 | 2/2007 | Blaeser et al. |
| 2007/0059258 A1 | 3/2007 | Chaudhuri |
| 2007/0092470 A1 | 4/2007 | Allef et al. |
| 2007/0128143 A1 * | 6/2007 | Gruning et al. ........... 424/70.12 |
| 2007/0134172 A1 | 6/2007 | Buchholz et al. |
| 2008/0038213 A1 | 2/2008 | Carola et al. |
| 2008/0145320 A1 | 6/2008 | Wenk et al. |
| 2008/0305056 A1 | 12/2008 | Jenni et al. |
| 2009/0054521 A1 | 2/2009 | Herrwerth et al. |
| 2009/0264657 A1 * | 10/2009 | Wagner et al. ............. 546/242 |
| 2010/0069505 A1 | 3/2010 | Veeger et al. |
| 2010/0294394 A1 | 11/2010 | Allef et al. |

FOREIGN PATENT DOCUMENTS

| | | |
|---|---|---|
| DE | 43 45 186 | 6/1995 |
| EP | 1 371 355 | 12/2003 |
| WO | 85 04101 | 9/1985 |
| WO | 99 65598 | 12/1999 |
| WO | 03 082239 | 10/2003 |
| WO | 2004 105712 | 12/2004 |
| WO | 2005 054222 | 6/2005 |
| WO | 2006 018104 | 2/2006 |

OTHER PUBLICATIONS

Arlamol HD safety data sheet.*
U.S. Appl. No. 12/446,569, filed Apr. 21, 2009, Veeger, et al.
U.S. Appl. No. 12/595,531, filed Oct. 12, 2009, Allef, et al.
U.S. Appl. No. 12/674,831, filed Feb. 23, 2010, Wenk, et al.
U.S. Appl. No. 12/933,835, filed Sep. 21, 2010, Allef, et al.
U.S. Appl. No. 13/379,489, filed Dec. 20, 2011, Thoerner, et al.
U.S. Appl. No. 13/380,064, filed Dec. 22, 2011, Allef, et al.

* cited by examiner

*Primary Examiner* — Sreeni Padmanabhan
*Assistant Examiner* — Svetlana M Ivanova
(74) *Attorney, Agent, or Firm* — Oblon, Spivak, McClelland, Maier & Neustadt, L.L.P.

(57) ABSTRACT

The invention relates to a silicone-free skin protection composition, in particular a composition to protect against cold, containing the components
  a.) at least one oil with a pour point in accordance with DIN ISO 30 16 of ≦−10° C.,
  b.) at least one polyol
  c.) at least one emulsifier
  d.) optionally at least one wax,
where the viscosity difference in the temperature interval from +4° C. to +50° C. of highest and lowest viscosity of the skin protection composition has a value in the range from 0 to ≦20 000 mPas.

2 Claims, 1 Drawing Sheet

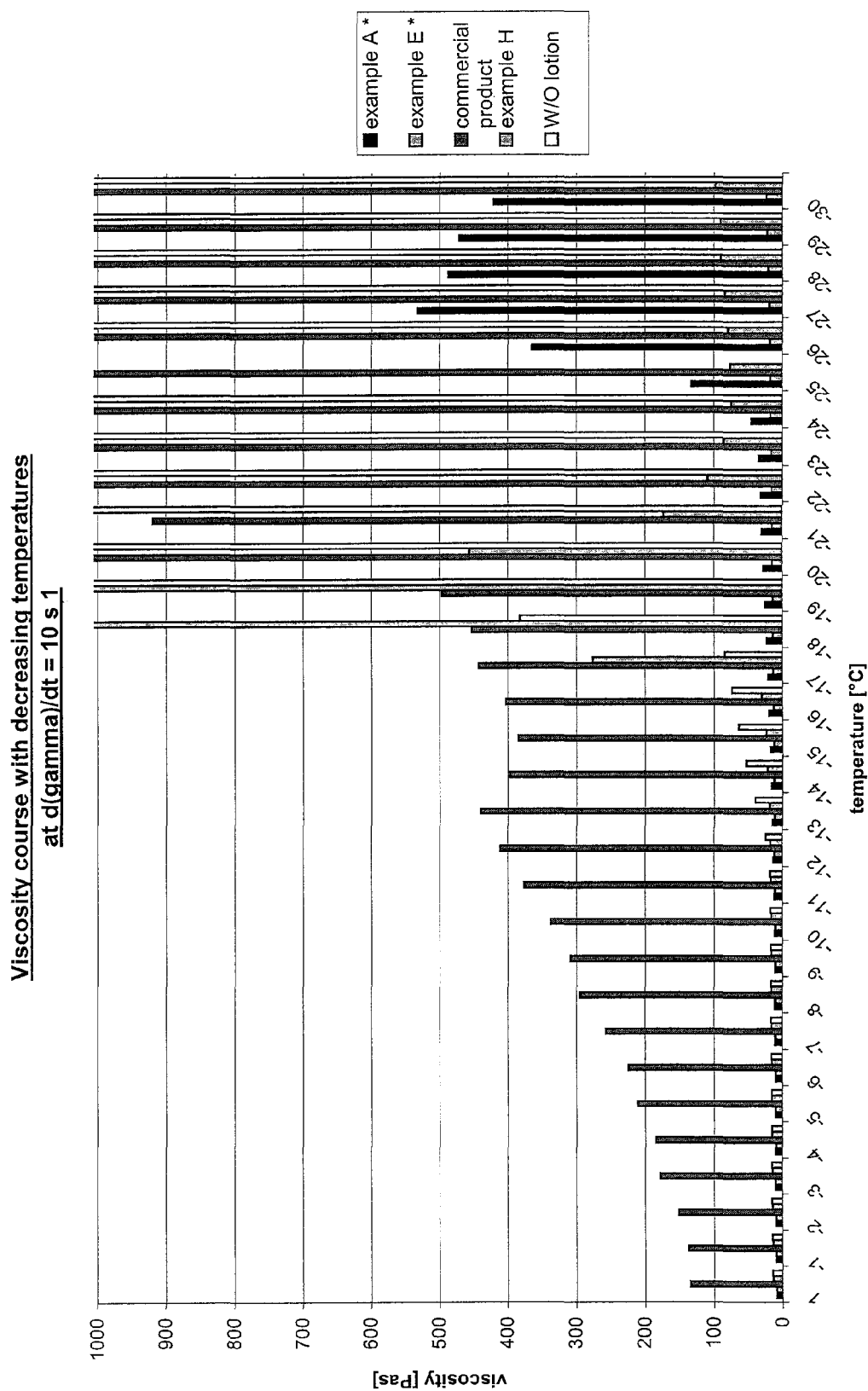

SKIN PROTECTION COMPOSITIONS, IN PARTICULAR CREAM TO PROTECT AGAINST COLD

The invention relates to a silicone-free skin protection composition, in particular a composition for protecting the skin in cases of extreme cold.

With a surface area of about 1.5 to 2.0 m$^2$, the human skin is the human organ of largest surface area which perceives functions vital to the body. For this purpose, the skin contains blood vessels and lymph vessels, through the walls of which the exchange of lymph fluid, gases, nutrients and waste materials can take place in order, for example, to ensure nutrition and metabolism. Further functions of the skin are the regulation of body temperature, protection of the body against drying out and against external mechanical, chemical and bacterial effects. Thus, the secretions from sebaceous glands in the skin keep the skin supple and help in regulating the water balance in the skin. Moreover, via free nerve endings, the skin conveys inter alia touch, heat and cold and pain sensations to the organism and thus has the function of the sensory organ.

The manifold products supplied for hygiene, body care and cosmetics, such as, for example, skin cleansing products, skin protection products and skincare products, therefore serve not only primarily for the cleansing, protection or care, respectively, of the skin, but they also maintain the quality of life and ensure a person's wellbeing.

Being the body sheath, the human skin represents the connection, but simultaneously also the boundary of the human body with its outside world. In particular, contact with everything which the human organism requires for life—but also that which can harm it—takes place via it.

Skin protection compositions are intended to protect the human skin from the very wide variety of dangers of the outside world, such as, for example, effects of the weather, water and aqueous solutions, chemicals, and soilings of any type. Usually, such skin protection compositions in anhydrous form cover the human skin with a "barrier" or protective film which cannot be absorbed by the skin. Ideally, this protective film is applied to the skin in such a way that its presence is not noticeable by those in the vicinity since it is invisible to them and/or cannot be felt by the user on his or her skin. In this connection, mention is to be made of skin protection preparations which are commercially available as "invisible glove" and which are to be used as completely water-impermeable barrier preparations when working with corrosive or aqueous toxic solutions and/or offer protection against organic solvents.

However, a disadvantage with such preparations is that the natural release of water vapour via the skin is impaired. On account of the associated build-up of heat and moisture, the acceptance for using such products by employees who daily often come into contact with aqueous and/or organic materials that are harmful to the skin is reduced.

Commercially, skin protection compositions are supplied in a large number in a very wide variety of preparation forms, for example in the form of sticks, salves, creams, jellies, as W/O emulsions, mixed emulsions and O/W emulsions, and as alcoholic lotions, which are then referred to, depending on the intended use and formulation, as sport oils or creams, all-weather creams, baby creams, skin protection salves, skin protection oils, but also fatty sticks, sunscreen compositions etc., with skin salves, skin creams, skin lotions, skin oils and skin gels being the most important types. Customary barrier agents in these skin protection preparations are primarily paraffin hydrocarbons such as mineral oils, vaseline etc., but also mineral and vegetable waxes including silicone oils and silicone waxes. Skin creams and skin lotions are based primarily on emulsions of the O/W type (oil-in-water) or W/O type (water-in-oil). Main constituents of the oil phase (also fatty or lipid phase) may then be fatty alcohols, fatty acids, fatty acid esters, waxes, vaseline, paraffins, but also other fats and oils, primarily of natural origin. Besides the emulsions of the O/W or W/O type customarily used for skin protection products, multiple emulsions are also known for the production of cosmetic and pharmaceutical products. Such multiple emulsions are emulsions of emulsions whose most important representatives multiple water/oil/water (W/O/W) and oil/water/oil (O/W/O) emulsions are described many times in the patent literature.

The aqueous phase can contain, inter alia, water-soluble care active ingredients which are moisture-regulating or moisture-retaining.

Which of the abovementioned emulsion types is used in a skin protection product depends primarily on which protection purpose is to be pursued by the product and/or against which working materials the product should protect.

To protect against the effects of the weather, e.g. extreme cold, inter alia in conjunction with strong winds, as are encountered for example, in the cold and desert regions of the northern and southern hemispheres, but also in the high alpine regions of the earth, use is made of anhydrous skin protection preparations. These are usually fatty creams with a high fraction of paraffins and fatty alcohols which protect the skin against moisture loss and heat loss. For this application, the abovementioned effect is utilized such that the applied protective film counteracts the natural release of water vapour, i.e. physiological skin breathing and, associated with this, temperature regulation of the skin.

The skin protection preparations which are intended for use in these regions also have to take into consideration these extreme weather conditions which prevail in the cold and desert regions of the earth. Thus, such preparations not only have to be able to withstand the extreme cold prevailing there, especially in winter, but in the short summers, temperatures up to 40° C. and above are also reached. In some arid climatic zones of the earth, the temperatures are >+40° C. in the daytime and drop to below 0° C. at night. These climatic conditions place high requirements on the stability and, associated therewith, the ability to transport and store such products. This applies all the more taking into consideration the fact that "freezing" of the products cannot be ruled out and, during the use period of such skin protection preparations, several cycles in which the products are frozen and then thawed again are to be assumed.

Many of the skin protection preparations currently on the market withstand these rigid climatic conditions only inadequately, especially with regard to their "freeze-thaw stability". Also, most products freeze completely at just −5° C. Since the cosmetic and pharmaceutical preparations of such products can no longer be removed from tubes at these low temperatures, they are supplied in the form of cans, pots etc. The application of such preparations is hard work, especially since the frozen product can only be spread on the skin with difficulty. Moreover, application from a tube is preferable to removal from a pot from a hygiene point of view.

It is known that the above problems can be solved using skin protection compositions based on silicones. For example, it is described that silicones, such as, for example, silicone oils and silicone waxes, are excellent barrier agents which have particular stability in skin protection compositions. They are resistant to heat and are extraordinarily resistant to the effect of corrosive chemicals. Moreover, such silicone-containing preparations are strongly hydrophobic and harmless to the skin because they are physiologically compatible, i.e. are not harmful to health, but instead are also skin-compatible. On account of the low surface tension of silicone oils, they can be spread easily on the skin. It is also advantageous that, in contrast to paraffins, vaseline etc., with silicone layers on the skin there is no risk of heat build-ups on the skin.

A disadvantage of such silicone-containing preparations, however, is that these preparations can leave behind residues on objects, for example on materials and/or workpieces, if such workpieces are passed by hand to a further operation. Thus, for example, those working with workpieces to be painted are unable to use such silicone-containing skin protection compositions since these very difficult to remove silicone residues are extremely bothersome in the further processing of these workpieces, such as, for example, painting or vulcanization, which lead in particular to painting flaws, such as, for example, paint wetting disturbances and/or crater formation on the workpieces. For this reason, especially in the automobile and coatings industry and also the rubber-processing industry, it is not possible to use silicone-containing skin protection products despite their excellent protective effect and acceptance.

There is thus a great need for silicone-oil-free skin protection compositions which not only exhibit good effectiveness during protection against the effects of the weather, water and aqueous solutions, chemicals and soilings, but which also have a profile of properties which adequately takes into consideration the conditions prevailing in the cold and desert regions of the earth, especially as regards transportability and storability and "freeze-thaw stability".

It was therefore an object of the present invention to develop such silicone-free skin protection compositions which can be used preferably in the form of a skin cream to protect against cold for so-called outdoor workers in the cold regions of the northern and southern hemispheres, but also in cold/skin-drying desert regions of the earth, in particular the compositions should still be able to be applied from a tube at at least −18° C., i.e. be pasty or flowable and/or spreadable and, moreover, the stability should be ensured over a period of at least 3 months at +40° or 1 month at +50° C., and also have a "freeze-thaw stability" of at least 3 freeze-thaw cycles.

Surprisingly, this object was achieved by a silicone-free skin protection composition, in particular compositions to protect against cold, which contain the components
 a.) at least one oil with a pour point in accordance with DIN ISO 30 16 of ≦−10° C.,
 b.) at least one polyol
 c.) at least one emulsifier
 d.) optionally at least one wax,
 where the viscosity difference in the temperature interval from +4° C. to +50° C. of highest and lowest viscosity of the skin protection composition has a value in the range from 0 to <20 000 mPas.

In one preferred embodiment the skin protection compositions have a viscosity difference in the temperature interval from +4° C. to +50° C. of highest and lowest viscosity of the skin protection composition with a value in the range of from 0 to ≦15 000 mPas and particularly preferably from 0 to ≦5000 mPas.

According to the invention, as component a.) it is possible to use any oil that is customarily used for cosmetic and/or pharmaceutical formulations which covers the skin with a protective or barrier film, in particular the paraffin hydrocarbons already specified above, such as mineral oils, for example vaseline etc., including vegetable and animal oils provided these do not lead, like, for example, the silicone-containing preparations, to undesired residues on materials and workpieces, either alone or as a mixture with one other or two or more other oils, if the oil or the oil mixture has a pour point according to DIN ISO 30 16 of ≦−10° C.

Oils of component a.) to be used with preference are hydrocarbons and carbonates, such as, for example,
Arlamol® HD (isohexadecane) from Uniqema, Gouda, Holland, pour point of −70° C.,
Paraffinum perliquidum, pour point of −15° C. or
Tegosoft® DEC (diethylhexyl carbonate) from Goldschmidt GmbH, Essen, Germany, pour point of −30° C.

Moreover, it is also possible to use other oils suitable for cosmetic and/or pharmaceutical formulations as component a.) if they are constituent of an oil mixture which satisfies the obligatory condition according to which the oil mixture has to have a pour point according to DIN ISO 30 16 of ≦−10° C.

By way of example, mention may be made here of Tegosoft® OS (ethylhexyl stearate), melting point of about 8° C.

Preferably, the oils of component a.) to be used are present in the skin protection compositions according to the invention in particular 10 to 50% by weight, based on the total composition of the skin protection composition, preferably 10 to 40% by weight and particularly preferably 15 to 30% by weight.

It is essential to the invention that the oils of component a.) are present in combination with at least one polyol of component b.) in the skin protection compositions according to the invention. It has been found that the skin protection compositions according to the invention, in particular in the form of a cream to protect against cold or W/O emulsion, which should still be able to be applied from a tube at at least −18° C., i.e. be pasty or flowable and/or spreadable, and, moreover, should ensure a stability over a period of at least 3 months at +40° or 1 month at +50° C., and should have a "freeze-thaw stability" of at least 3 freeze-thaw cycles, are not obtained through the use of oils or oil mixtures with a pour point according to DIN ISO 30 16 of <−10° C. on their own.

Suitable polyols of component b.), which can be used on their own or as a mixture with one further or two or more other polyols, are customary polyalcohols and polyhydroxy compounds, preferably having 2 to 15 carbon atoms and at least 2 hydroxyl groups suitable, i.e. physiologically compatible, for cosmetic and/or pharmaceutical formulations. By way of example, mention may be made here of polyhydric alcohols, such as straight-chain, branched or cyclic alkanols having 2 to 15, preferably 2 to 6, carbon atoms, where glycerol and/or 1,2-propanediol are particularly preferred. Moreover, glycols, such as, for example, polyethylene glycols, polypropylene glycols, but also sugars and sugar derivatives, preferably fructose, glucose, sucrose, sugar alcohols, in particular sorbitol, mannitol, etc., may be present in the skin protection compositions according to the invention. The fraction of component b.) in the skin protection compositions is here at least 7.5 to 40% by weight, based on the total composition of the skin protection composition, preferably 10 to 35 and particularly preferably 15 to 25% by weight.

Furthermore, the skin protection compositions according to the invention comprise 1 to 10% by weight, preferably 2 to 8% by weight, particularly preferably 2 to 4% by weight, based on the total composition of the skin protection composition, of at least one emulsifier, which may be present on its own or as a mixture with one further or two or more other emulsifiers.

According to the invention, esters of polyhydroxystearic acid and/or of polyricinoleic acid are preferred for the skin protection compositions according to the invention as emulsifiers. Particular preference is given to polyglycerol partial esters of polyhydroxystearic acid and polyfunctional carboxylic acids which are obtainable by esterification a.) of a polyglycerol mixture with
b.) polyhydroxystearic acid and
c.) di- and/or tricarboxylic acids and if desired/or with
d.) dimer fatty acids, and
e.) fatty acids having 6 to 22 carbon atoms, the preparation of which is described in DE 103 33 443 A1, to the entire contents of which reference is made and hereby incorporated into the description of this patent application.

Emulsifiers of component c.) particularly preferred according to the invention are polyglycerol partial esters of polyhydroxystearic acid which are obtainable from Goldschmidt GmbH, Essen under the name ISOLAN® GPS (polyglyceryl-4 diisostearate polyhydroxystearate sebacate). Further commercially available emulsifiers, in particular based on polyhydroxystearic acid and/or polyricinoleic acid, are Crester® PR (polyglyceryl-3 ricinoleate) from Croda, Dehymuls® PGPH (polyglyceryl-2 dipolyhydroxystearate) from Cognis, and Arlacel® P135 (PEG-30 dipolyhydroxystearate) or Arlacel® 1689V (polyglyceryl-3 polyricinoleate) from Uniqema, which may be present according to the invention in the products according to the invention in the range from 1 to 10% by weight, preferably 2 to 4% by weight, based on the total composition of the skin protection composition, either alone or as an emulsifier mixture.

Moreover, further coemulsifiers can be added to the emulsifier mixture. In particular, the emulsifier mixture can additionally comprise at least one alkyl and/or alkylene glucoside and a fatty alcohol and/or partial glycerides and optionally further coemulsifiers. Such emulsifiers are described in DE 196 12 084 A1, to the entire contents of which reference is made and which are hereby likewise incorporated into the description of this patent application.

Optionally, the skin protection compositions according to the invention contain, as component d.), up to at most 2% by weight, preferably up to 0.25 to 1% by weight, of at least one wax, which may be present either on its own or as a mixture with one further or two or more other waxes, such as, for example, vegetable and/or animal waxes, in particular candelilla wax, carnauba wax, Japan wax, esparto wax, cork wax, rice germ oil wax, guaruma wax, ouricury wax, montan wax, jojoba wax, shea butter, berry wax, beeswax, shellac wax, spermaceti, lanolin, uropygial grease, mineral waxes, such as, for example, ceresin or ozokerite (earth wax), petrochemical waxes, in particular petrolatum, paraffin waxes, and microcrystalline waxes. Moreover, chemically modified waxes and synthetic waxes may also be present as component d.) in the skin protection compositions according to the invention, in particular also montan ester waxes, sasol waxes, hydrogenated jojoba waxes, polyalkylene waxes, polyethylene glycol waxes, but also chemically modified fats, such as, for example, hydrogenated vegetable oil, in particular hydrogenated castor oil, hydrogenated coconut fatty glycerides, triglycerides etc. The skin protection compositions according to the invention particularly preferably contain hydrogenated castor oil, which is sold, for example, under the trade name CUTINA® HR by Cognis, or mineral waxes, such as, for example, ceresin, which may be obtained as microcrystalline wax under the trade name Paracera® W 80.

Besides water, the silicone-free skin protection compositions according to the invention can if desired contain auxiliaries, additives and/or active ingredients, such as, for example, dyes, solubility promoters, complexing agents, sequestrants, photo-protective filters or fragrances, pH regulators, stabilizers, preferably cetearyl alcohol and/or hydrogenated castor oils, such as, for example, trihydroxystearin, preservatives, antioxidants and/or oily or aqueous care components as further components, in particular in the amounts customary for cosmetic and/or pharmaceutical formulations of from preferably 0.05 to 30% by weight, based on the total weight of the skin protection composition, the person skilled in the art choosing the weight fraction of these components such that there is no resulting adverse effect on the barrier formation of the skin protection compositions according to the invention on account of possible penetration-promoting properties of these auxiliaries, additives and/or active ingredients.

According to the invention, preference is given to silicone-free skin protection compositions, in particular compositions to protect against cold, in the form of W/O emulsions, which contain the components, in each case based on the total composition of the skin protection composition, a.) at least 10 to 50% by weight of at least one oil with a pour point according to DIN ISO 30 16 of $\leq -10°$ C.,
b.) at least 10 to 40% by weight of at least one polyol,
c.) at least 1 to 10% by weight of at least one emulsifier,
d.) optionally up to at most 2% by weight of at least one wax, with the proviso that the amounts add up to 100% by weight with water and any further additives.

The skin protection compositions according to the invention can be used particularly advantageously to protect against extreme climatic effects of the weather, as are encountered in the cold and desert regions of the northern and southern hemispheress, but also in the high alpine regions of the earth. Surprisingly, it has thus been found that the formulations according to the invention counteract very well the skin drying which prevails in these climates although these formulations have an oil content which is rather low compared with standard commercial products, such as, for example, creams that protect against cold. Furthermore, it is known to the person skilled in the art that polyols on their own generally remove water from the skin in a cold climate, meaning that their use in formulations to protect against cold is actually to be considered as nonconducive to the aim because their use in compositions to protect against cold appears to be an obstacle to the desired profile of requirements.

Moreover, the products according to the invention not only offer, as already explained, protection against the weather conditions prevailing in these climates, in particular extreme cold inter alia in conjunction with strong winds, and they also have improved transportability and storability, including improved "freeze-thaw stability", but they can also still be applied from a tube at at least −18° C., i.e. are pasty or flowable and spreadable and can be spread on the skin even at these temperatures. Thus, the products according to the invention have at T=−18° C. viscosities of about 20 000 mPas and particularly advantageously the viscosities at a temperature of −24° C. are still less than 50 000 mPas, in particular the viscosity course as the temperature decreases—determined according to the method in G. Schramm; "Einführung in die praktische Viskosimetrie" [Introduction to practical viscometry]; 1981, Gebrüder Haake GmbH, 5th edition (see experimental section)—shows at $d(\gamma)/dt=10$ $s^{-1}$, that a viscosity maximum of at most 600 Pas is not exceeded in the temperature interval under any circumstances.

In particular, it is also particularly advantageous that they are stable over a period of at least 3 months at +40° C. or at least 1 month at +50° C. and have a "freeze-thaw stability" of at least 3 freeze-thaw cycles.

On account of this profile of properties, the skin protection compositions according to the invention are especially suitable for so-called outdoor workers, such as, for example, those employed in the exploration of petroleum and natural gas, in particular on petroleum platforms, for example in the North Sea, and also in the mining industry, in the cold regions of the northern and southern hemispheress, but also in the cold/skin-drying desert regions of the earth. Examples which may be mentioned here are the regions of Alaska, Siberia and central Asia which are rich in raw materials. Particularly preferably, the skin protection compositions according to the invention can also be used in the commercial sector for prolonged working in chilled/frozen storage depots.

Furthermore, it is advantageous that the skin protection compositions according to the invention in particular offer protection against aqueous noxae, so that they can be used as protective compositions, for example, for workplaces such as, for example, in the metal processing, rubber-processing industries, since an adverse effect on working processes by residues of silicone compounds, for example on materials or workpieces, can be excluded.

The skin protection compositions according to the invention can likewise be used in agriculture and forestry, but also for corresponding leisure and hobby activities, such as, for example, winter sports and mountaineering, especially in extreme weather conditions, for example as so-called all-weather creams, sport oils or creams etc.

The invention is explained below by reference to examples. These explanations are merely exemplary and do not limit the invention present here. Unless stated otherwise, the stated quantitative data, fractions and percentages are based on the weight and on the total amount or on the total weight of the skin protection compositions according to the invention.

Experimental Section:

1. Pour Point Determination:

The pour point determination for the oils of component a.) present in the skin protection compositions according to the invention was carried out in accordance with DIN ISO 3016 October 1982.

According to this standard, the pour point is defined as the temperature, i.e. lowest temperature, at which an oil or oil mixture just still flows.

For this, in accordance with the conditions stipulated in DIN ISO 3016, an oil sample, with prior heating, is cooled in a controlled manner, the oil sample being tested for its flowability in temperature intervals of 3° C. in each case until the temperature of the pour point is reached for the particular sample.

2. Viscosity Determination:

The viscosity values determined for the skin protection compositions according to the invention were obtained using a viscometer from Brookfield Engineering Inc., namely a Brookfield RVT rotary viscometer with spindle set 1-7.

The skin protection compositions according to the invention are produced by means of customary known devices and processes, the skin protection compositions preferably being obtained as creamy compositions or as flowable viscous pastes, in particular particularly preferably as W/O emulsions.

Skin protection compositions preferred according to the invention, in particular creams to protect against cold with the exception of Comparative Examples H, I and J have, for example, the following compositions:

| Raw material | A | B | C | D | E | F | G | H | I | J |
|---|---|---|---|---|---|---|---|---|---|---|
| Isolan ® GPS | 3.0 | 5.0 | 7.0 | 10 | 3.0 | 3.0 | 3.0 | 3.0 | 3.0 | 3.0 |
| Cutina ® HR | 0.5 | 0.5 | 0.5 | 0.5 | 0.5 | 0.5 | 0.5 | 0.25 | 0.25 | 0.5 |
| Paracera ® W 80 | 0.5 | 0.5 | 0.5 | 0.5 | 0.5 | 0.5 | 0.5 | 0.25 | 0.25 | 0.5 |
| Isohexadecane | 5.0 | 5.0 | 5.0 | 5.0 | 10.7 | 10.7 | 10.7 | 5.0 | 10.7 | 10.7 |
| Ethylhexyl stearate | 5.8 | 5.8 | 5.8 | 5.8 | | | | 5.8 | | |
| Tegosoft ® DEC | 5.0 | 5.0 | 5.0 | 5.0 | 10.0 | | 10.0 | 5.0 | 10.0 | 10.0 |
| Paraffinum perliquidum | | | | | 10.0 | 10.0 | 10.0 | | 10.0 | 10.0 |
| Sorbitol | 10.0 | 10.0 | 10.0 | 10.0 | 10.0 | 10.0 | 5.0 | 5.0 | | |
| Glycerol | 10.0 | 10.0 | 10.0 | 10.0 | 10.0 | 10.0 | 5.0 | 5.0 | 2.0 | 2.0 |
| Propylene glycol | 4.0 | 4.0 | 4.0 | | | | | | 3.0 | 3.0 |
| Panthenol | | | | | 0.6 | | | | | |
| Allantoin | | | | | 0.4 | | | | | |
| Phenoxyethanol | | | | | 1.0 | | | | | |
| MgSO$_4$ × 7 H$_2$O (bitter salt) | | | | | 1.5 | | | | | |
| Perfume | | | | | 0.2 | | | | | |
| Water | | | | | ad 100 | | | | | |

| Raw material | K | L | M | N | O | P | Q | R |
|---|---|---|---|---|---|---|---|---|
| Crester ® PR | 3.0 | 5.0 | 7.0 | 10.0 | | | | |
| Arlacel ® 1689 V | | | | | 3.0 | 5.0 | 7.0 | 10.0 |
| Cutina ® HR | 0.5 | 0.5 | 0.5 | 0.5 | 0.5 | 0.5 | 0.5 | 0.5 |
| Paracera W 80 | 0.5 | 0.5 | 0.5 | 0.5 | 0.5 | 0.5 | 0.5 | 0.5 |
| Isohexadecane | 5.0 | 5.0 | 5.0 | 5.0 | 5.0 | 5.0 | 5.0 | 5.0 |
| Ethylhexyl stearate | 5.8 | 5.8 | 5.8 | 5.8 | 5.8 | 5.8 | 5.8 | 5.8 |
| Tegosoft ® DEC | 5.0 | 5.0 | 5.0 | 5.0 | 5.0 | 5.0 | 5.0 | 5.0 |
| Paraffinum perliquidum | | | | | | | | |
| Sorbitol | 10.0 | 10.0 | 10.0 | 10.0 | 10.0 | 10.0 | 10.0 | 10.0 |
| Glycerol | 10.0 | 10.0 | 10.0 | 10.0 | 10.0 | 10.0 | 10.0 | 10.0 |
| Propylene glycol | 4.0 | 4.0 | 4.0 | | 4.0 | 4.0 | 4.0 | |
| Panthenol | | | | 0.6 | | | | |

-continued

| Raw material | K | L | M | N | O | P | Q | R |
|---|---|---|---|---|---|---|---|---|
| Allantoin | | | | 0.4 | | | | |
| Phenoxyethanol | | | | 1.0 | | | | |
| MgSO$_4$ × 7 H$_2$O (bitter salt) | | | | 1.5 | | | | |
| Perfume | | | | 0.2 | | | | |
| Water | | | | ad 100 | | | | |

It could be shown experimentally that the use of low-boiling oils as, for example, in Example I on their own does not lead to the formulations according to the invention with the desired profile of requirements, according to which the compositions must still be able to be applied from a tube at at least −18° C., i.e. be pasty and flowable and/or spreadable, and the stability is ensured over a period of at least 3 months at +40° C. or 1 month at +50° C. coupled with a "freeze-thaw stability" of at least 3 freeze-thaw cycles. Thus, the formulation according to Example I was water-thin at room temperature and was finally unstable at 40° C. At −20° C., the formulation was completely frozen and no longer spreadable.

Even increasing the wax content according to Example J did not lead to products with the abovementioned profile of requirements. At −20° C., the formulation was likewise completely frozen and no longer spreadable.

The same is true if, according to Example H, the oil content is reduced, thus, although a smooth cream is obtained at room temperature, which also remains stable at high temperatures, this formulation freezes even at below −5° C.

The formulation according to Example E according to the invention has a viscosity of 3000 mPas at 4° C. and a viscosity of 2500 mPas at 50° C. and it has a viscosity of 40 000 mPas at −18° C. (measured using Brookfield RVT rotary viscometer with spindle set 1-7).

3. Determination of the Applicability, i.e. the Pasticity and Flowability and/or Spreadability of the Skin Protection Compositions According to the Invention The applicability of the skin protection compositions according to the invention and of the comparison products was determined according to G. Schramm; "Ein-führung in die praktische Viskosimetrie" [Introduction to practical viscometry]; 1981, Gebrüder Haake GmbH, 5th edition.

According to this, upon squeezing a cream from a tube with an opening diameter of 5 mm assuming a constant, laminar flow rate of Q=1 (cm/s), a velocity gradient $d(\gamma)/dt$ of 81 (s$^{-1}$) is achieved—at an opening diameter of 4 mm as much as 159 (s$^{-1}$). This corresponds to the formula: $D=4/\pi*Q/R^3$
D=velocity gradient $d(\gamma)/dt$
Q=flow rate cm/s
R=tube opening radius The shear stress T here is a parameter dependent on the viscosity $\eta$ of the substance. It is defined as T=force/area=$\eta*D$. At a constant velocity gradient, T is directly proportional to $\eta$.

According to the invention, the ability of a skin protection composition to be squeezed out of a tube is equated with applicability, i.e. pasticity or flowability and/or spreadability. This method was chosen because with it it is possible to determine the ability of a flowable medium to be squeezed out of a tube, so that the criterion according to the invention, according to which the compositions according to the invention still have to be able to be applied from a tube at at least −18° C., preferably at at least −20° C., i.e. be pasty and flowable and/or spreadable, can be verified and thus also ensured.

According to this method, when rubbing in a handcream, velocity gradients between D=10 000-20 000 (s$^{-1}$) are achieved.

The measurements of various formulations at discrete temperatures between +20° C. and −30° C. were carried out using a Physica MCR 301 oscillation rheometer from Anton Paar.

The table below and the associated diagram show, by way of example, the measurements of inventive and noninventive formulations and of a commercial product which have been carried out at a constant velocity gradient of $d(\gamma)/dt=10$ s$^{-1}$:

Viscosity Course in [Pas]

| Temperature | Example A | Example E | Commercial product | Example H | W/O lotion |
|---|---|---|---|---|---|
| 1 | 8.94 | 8.96 | 134 | 13.6 | 14 |
| −1 | 9.15 | 9.11 | 137 | 13.7 | 14.3 |
| −2 | 9.26 | 9.28 | 151 | 13.9 | 14.6 |
| −3 | 9.42 | 9.44 | 178 | 14.3 | 14.9 |
| −4 | 9.7 | 9.62 | 185 | 15 | 15.3 |
| −5 | 9.7 | 9.81 | 211 | 15.3 | 15.6 |
| −6 | 9.51 | 9.99 | 224 | 15.6 | 16 |
| −7 | 10.1 | 10.2 | 257 | 15.8 | 16.4 |
| −8 | 10.5 | 10.4 | 294 | 16.1 | 16.8 |
| −9 | 10.8 | 10.6 | 309 | 16.4 | 17.2 |
| −10 | 11 | 10.8 | 337 | 16.7 | 17.7 |
| −11 | 11.4 | 11.1 | 376 | 17 | 18.2 |
| −12 | 12.8 | 11.3 | 411 | 17.4 | 24.5 |
| −13 | 14.7 | 11.7 | 440 | 19.5 | 40.2 |
| −14 | 16.4 | 12 | 397 | 21.9 | 52.7 |
| −15 | 18 | 12.4 | 384 | 24.1 | 63.6 |
| −16 | 19.8 | 12.8 | 403 | 30.1 | 73.9 |
| −17 | 21.1 | 13.2 | 443 | 276 | 84.3 |
| −18 | 23.6 | 13.6 | 453 | 549000 | 382 |
| −19 | 25.3 | 14.1 | 496 | 1640* | 67000000 |

-continued

| Temperature | Example A | Example E | Commercial product | Example H | W/O lotion |
|---|---|---|---|---|---|
| −20 | 27.6 | 14.6 | 1050 | 456* | 341000000 |
| −21 | 29.6 | 15.2 | 920 | 173* | 1340000000 |
| −22 | 31.9 | 15.7 | 1050 | 109* | 1740000000 |
| −23 | 34.7 | 16.4 | 1360 | 85.5* | 1840000000 |
| −24 | 44.8 | 17.1 | 2020 | 74.5* | 959000000 |
| −25 | 132 | 17.8 | 16700 | 76* | −11300000000 |
| −26 | 364 | 18.6 | 34900 | 79.2* | 2270000000 |
| −27 | 532 | 19.5 | 102000 | 84.6* | 7010000000 |
| −28 | 487 | 20.9 | 446000 | 89.8* | 4020000000 |
| −29 | 471 | 22 | 1900000 | 89.9* | 3560000000 |
| −30 | 421 | 23.4 | 7550000 | 97.5* | 1710000000 |

*Product was unstable at this temperature

The table and the associated diagram reveal that the formulations according to the invention have, at T=−18° C., viscosities of about 20 000 mPas and particularly advantageously at a temperature of −24° C. are still less than 50 000 mPas. Moreover, the viscosity maximum in the case of the formulations according to the invention is at most 600 Pas in the temperature range to −30° C.

The invention claimed is:

1. A silicone-free composition that consists essentially of:
   (a) 10 to 50 wt. % of at least one oil with a pour point of ≦−10° C. in accordance with DIN ISO 30 16,
   (b) 15 to 40 wt. % of at least one polyol having 2 to 15 carbon atoms and at least two hydroxyl groups,
   (c) 1 to 10 wt. % of at least one emulsifier, and
   (d) up to 2 wt. % of at least one wax;
   wherein said silicone-free composition is stable and has a viscosity of at most 600 Pas within a temperature range between 1° C. and −30° C. as determined by a constant velocity gradient of $d(\gamma)/dt=10\ s^{-1}$.

2. A silicone-free composition that consists essentially of:
   (a) 10 to 50 wt. % of at least one oil with a pour point of ≦−10° C. in accordance with DIN ISO 30 16,
   (b) 15 to 40 wt. % of at least one polyol having 2 to 15 carbon atoms and at least two hydroxyl groups,
   (c) 1 to 10 wt. % of at least one emulsifier, and
   (d) up to 2 wt. % of at least one wax; and
   (e) water;
   wherein said silicone-free composition is stable and has a viscosity of at most 600 Pas within a temperature range between 1° C. and −30° C. as determined by a constant velocity gradient of $d(\gamma)/dt=10\ s^{-1}$.

* * * * *